(12) United States Patent
Haji Reza et al.

(10) Patent No.: US 10,627,338 B2
(45) Date of Patent: Apr. 21, 2020

(54) CAMERA-BASED PHOTOACOUSTIC REMOTE SENSING (C-PARS)

(71) Applicant: ILLUMISONICS INC., Edmonton (CA)

(72) Inventors: Parsin Haji Reza, Edmonton (CA); Roger Zemp, Edmonton (CA)

(73) Assignee: illumiSonics Inc., Edmonton, Alberta ( * ) Notice: Subject to any disclaimer, the term of this patent is extended or adjusted under 35 U.S.C. 154(b) by 0 days.

(21) Appl. No.: 15/933,193

(22) Filed: Mar. 22, 2018

(65) Prior Publication Data

US 2018/0275046 A1 Sep. 27, 2018

Related U.S. Application Data

(60) Provisional application No. 62/475,693, filed on Mar. 23, 2017.

(51) Int. Cl.
| | | |
|---|---|---|
| G01N 21/00 | (2006.01) | |
| G01N 21/17 | (2006.01) | |
| G01N 21/49 | (2006.01) | |
| A61B 90/00 | (2016.01) | |
| A61B 5/00 | (2006.01) | |
| G01N 21/47 | (2006.01) | |

(Continued)

(52) U.S. Cl.
CPC ....... *G01N 21/1702* (2013.01); *A61B 5/0095* (2013.01); *A61B 90/361* (2016.02); *G01N 21/1717* (2013.01); *G01N 21/4795* (2013.01); *G01N 21/49* (2013.01); *A61B 5/026* (2013.01); *A61B 5/14542* (2013.01); *G01N 2021/1706* (2013.01); *G01N 2021/1725* (2013.01)

(58) Field of Classification Search
CPC .... G01N 21/534; G01N 21/59; G01N 21/255; G01J 3/42; G01J 1/16
USPC .......................................... 356/434
See application file for complete search history.

(56) References Cited

U.S. PATENT DOCUMENTS

| 5,479,259 A | 12/1995 | Nakata et al. |
|---|---|---|
| 2009/0170149 A1 | 7/2009 | Viator et al. |

(Continued)

FOREIGN PATENT DOCUMENTS

| CN | 103048271 A | 4/2013 |
|---|---|---|
| DE | 10 2010 012 809 A1 | 9/2011 |

(Continued)

OTHER PUBLICATIONS

International Search Report and Written Opinion dated Dec. 19, 2018 in International Application No. PCT/IB2018/057565 (25 pages).

(Continued)

*Primary Examiner* — Md M Rahman
(74) *Attorney, Agent, or Firm* — Bookoff McAndrews, PLLC (57) ABSTRACT

A camera-based photoacoustic remote sensing system (C-PARS) for imaging a subsurface and deep structures in a sample, has an excitation beam configured to generate ultrasonic signals in the sample at an excitation location; an interrogation beam incident on the sample at the excitation location, a portion of the interrogation beam returning from the sample that is indicative of the generated ultrasonic signals; a camera to map the returning portion of the interrogation beam over the entire field of view.

27 Claims, 5 Drawing Sheets

(51) Int. Cl.
*A61B 5/145* (2006.01)
*A61B 5/026* (2006.01)

(56) References Cited

U.S. PATENT DOCUMENTS

| | | | |
|---|---|---|---|
| 2012/0200845 A1* | 8/2012 | Rousseau | A61B 5/0093 |
| | | | 356/72 |
| 2014/0009808 A1 | 1/2014 | Wang et al. | |
| 2014/0185055 A1 | 7/2014 | Wang | |
| 2015/0077819 A1* | 3/2015 | Schnell | G03H 1/14 |
| | | | 359/9 |
| 2016/0113507 A1* | 4/2016 | Reza | G01N 21/1717 |

FOREIGN PATENT DOCUMENTS

| | | | |
|---|---|---|---|
| WO | 2009/055705 A2 | 4/2009 | |
| WO | 2014/036405 A2 | 3/2014 | |

OTHER PUBLICATIONS

Kevan L. Bell et al., "Coherence-gated photoacoustic remote sensing microscopy", Optics Express, vol. 26, No. 18, Sep. 3, 2018, 16 pp.

Zhihua Ding et al., "Real-time phase-resolved optical coherence tomography and optical Doppler tomography", Optics Express, vol. 10, No. 5, Mar. 11, 2002, 10 pages.

Cedric Blatter et al., "Intrasweep phase-sensitive optical coherence tomography for noncontact optical photoacoustic imaging", Optics Letters, vol. 37, No. 21, Nov. 1, 2012, 4 pp.

* cited by examiner

CAMERA-BASED PHOTOACOUSTIC REMOTE SENSING (C-PARS)

FIELD

This relates to the field of biomedical optics imaging and, in particular, to a laser and ultrasound-based method and system for in vivo or ex vivo, non-contact imaging of biological tissue.

BACKGROUND

Photoacoustic imaging is an emerging hybrid imaging technology providing optical contrast with high spatial resolution. Nanosecond or picosecond laser pulses fired into tissue launch thermo-elastic-induced acoustic waves which are detected and reconstructed to form high-resolution images. Photoacoustic imaging has been developed into multiple applications, including photoacoustic tomography (PAT), photoacoustic microscopy (PAM), optical-resolution photoacoustic microscopy (OR-PAM), and array-based PA imaging (array-PAI). In photoacoustic tomography (PAT) signals are collected from multiple transducer locations and reconstructed to form a tomographic image in a way similar to X-ray CT. In PAM, typically, a single element focused high-frequency ultrasound transducer is used to collect photoacoustic signals. A photoacoustic signal as a function of time (depth) is recorded for each position in a mechanically scanned trajectory to form a 3-D photoacoustic image. The maximum amplitude as a function of depth can be determined at each x-y scan position to form a maximum amplitude projection (MAP) C-scan image. Photoacoustic microscopy has shown significant potential for imaging vascular structures from macro-vessels all the way down to micro-vessels. It has also shown great promise for functional and molecular imaging, including imaging of nanoparticle contrast agents and imaging of gene expression. Multi-wavelength photoacoustic imaging has been used for imaging of blood oxygen saturation, by using known oxy- and deoxy-hemoglobin molar extinction spectra.

In traditional photoacoustic imaging, spatial resolution is due to ultrasonic focusing and can provide a depth-to-resolution ratio greater than 100. In OR-PAM, penetration depth is limited to ~1 mm in tissue (due to fundamental limitations of light transport) but resolution is micron-scale due to optical focusing. OR-PAM can provide micron-scale images of optical absorption in reflection-mode, in vivo, something that no other technique can provide. OR-PAM is capable of imaging blood vessels down to capillary size noninvasively. Capillaries are the smallest vessels in the body and much crucial biology occurs at this level, including oxygen and nutrient transport. Much can go wrong at the capillary level too. In cancers, cells have an insatiable appetite for oxygen and nutrients to support their uncontrolled growth. They invoke a range of signaling pathways to spawn new vessels in a process known as angiogenesis and these vessels typically form abnormally. Tumors are often highly heterogeneous and have regions of hypoxia. Photoacoustic imaging has demonstrated the ability to image blood oxygen saturation (SO2) and tumor hypoxia in vivo.

In most photoacoustic and ultrasound imaging systems, piezoelectric transducers have been employed, in which an ultrasound coupling medium such as water or ultrasound gel is required. However for many clinical applications such as wound healing, burn diagnostics, surgery, and many endoscopic procedures physical contact, coupling, or immersion is undesirable or impractical.

The detection of ultrasound in photoacoustic imaging has, until recently, relied on ultrasonic transducers in contact with the biological tissue or an ultrasonic coupling agent both of which have major drawbacks as described above. Some detection strategies to solving the non-contact optical interferometric sensing problems associated with photoacoustic imaging have been reported.

Optical means of detecting ultrasound and photoacoustic signals have been investigated over a number of years; however, to date no technique has demonstrated practical non-contact in vivo microscopy in reflection mode with confocal resolution and optical absorption as the contrast mechanism.

Most previous approaches detected surface oscillations with interferometric methods. Others used interferometry to observe photoacoustic stresses, including optical coherence tomography (OCT) methods. These methods offer potential sensitivity to the scattered probe beam phase modulations associated with motion of scatterers, subsurface and surface oscillations, as well as unwanted vibrations. They are also sensitive to complex amplitude reflectivity modulations. The net interferometric signal may be a mixture of these composite mechanisms and could lead to unwanted interference.

One example of a low-coherence interferometry method for sensing photoacoustic signals was proposed in U.S. pregrant publication no. 2014/0185055 to be combined with an optical coherence tomography (OCT) system, resulting in 30 µm lateral resolution.

Another prior art system is described in U.S. pregrant publication no. 2012/0200845 entitled "Biological Tissue Inspection Method and System", which describes a noncontact photoacoustic imaging system for in vivo or ex vivo, non-contact imaging of biological tissue without the need for a coupling agent.

Other systems use a fiber based interferometer with optical amplification to detect photoacoustic signals and form photoacoustic images of phantoms with acoustic (not optical) resolution. However these systems suffer from a poor signal-to-noise ratio, other contact-based photoacoustic systems offer significantly improved detection capabilities, in vivo imaging was not demonstrated, and optical-resolution excitation was not demonstrated.

Industrial laser ultrasonics has used interferometry to detect acoustic signatures due to optical excitation of inanimate objects for non-destructive testing. This approach has been adapted to detect ultrasound ex vivo in chicken breast and calf brain specimens, however, optical-resolution focusing of the excitation light was not examined.

Laser Doppler vibrometry has been a powerful non-contact vibration sensing methodology, however, weak signal-to-noise and poor image quality have proven to be a limitation when sensing deep-tissue signals from broad-beam photoacoustic excitation.

Similarly, Mach Zehnder interferometry and two-wave mixing interferometry have been used previously for sensing photoacoustic signals. However many such techniques still require direct contact or fluid coupling; have not offered in vivo studies or optical resolution for phantom studies.

The previous photoacoustic detection methods are based on ultrasound transducers or optical sensing in which a photodiode is responsible for detecting photoacoustic signals. In these methods the field of view, imaging depth, resolution and the speed of imaging are limited.

SUMMARY

There is provided a mechanism for sensing optical absorption using pulsed-excitation-induced changes in optical scattering and reflection. These changes are observable without any need for phase-sensitive optical detection methods, which may be referred to as C-PARS (Camera-Based Photoacoustic Remote Sensing).

Previously, tightly focused excitation and interrogation beams co-focused and co-scanned have been used to map out PARS images with optical absorption contrast. Absorption-induced scattering changes were detected by observing time-varying changes in the interrogation beam as detected by a photodiode. C-PARS is the extension of previous methods, such as Photoacoustic Remote Sensing [PARS] and Non-interferometric Photoacoustic Sensing [NI-PARS] in which a non-interferometric method is used to collect the absorption-induced changes in reflected light on a camera or array of cameras using gated observations.

C-PARS is fundamentally different from other detection methods, since a non-contact method is used to map the amount of reflected light from the sample due to generated photoacoustic signal on a camera.

C-PARS enables reflection-mode imaging of optical absorption in a non-contact way, unlike most previous photoacoustic imaging systems which require acoustic coupling to an ultrasound transducer. Additionally, most photoacoustic imaging systems do not enable visualization of the imaging area by eye or by camera as the imaging probe obstructs the view. C-PARS enables both imaging of scattered light from object surfaces as well as imaging of absorption-induced changes of the scattered light. C-PARS enables wide-field of view imaging with a single excitation pulse, unlike previous PARS microscopy systems and unlike most photoacoustic imaging platforms.

Compared to acoustic-resolution PAM, C-PARS offers the advantage of finer optical resolution, non-contact detection and real-time wide field planar C-scan imaging. Compared to OR-PAM, C-PARS offers the advantage of non-contact imaging without the need for an ultrasound transducer, and enables fast single-shot imaging over an entire field of view. Compared to other all-optical ultrasonic detection schemes (such as Fabry-Perot etalons, Micro-ring resonators, etc.) our C-PARS technology requires no additional device and offers non-contact imaging with much faster imaging speed over an entire field-of-view. Compared to other non-contact all-optical detection methods, such as those described in U.S. pregrant pub. no. 2014/0185055 and 2012/0200845, this approach offers faster acquisition and a different phase-incoherent detection mechanism. Additionally, an entire field-of-view is imaged owing to a camera-based detector array. The approach in US2012/0200845 used a large-excitation spot and scanned a focused interrogation beam, detecting surface oscillations using phase-sensitive methods. Our approach instead detects pulsed-absorption-induced scattering changes and not surface oscillations. The approach in US2014/0185055 detects surface oscillations with optical coherence tomography (OCT). The presently described approach does not use OCT and as mentioned is capable of single-excitation pulse imaging over an entire field of view, unlike their method.

According to an aspect, there is provided a C-PARS for imaging structures in a sample, where the C-PARS comprises an excitation beam configured to generate ultrasonic signals in the sample at an excitation location; an interrogation beam is incident on the sample at the excitation location; a portion of the interrogation beam returning from the sample is indicative of the generated ultrasonic signals; a camera detects the returning portion of the interrogation beam.

According to other aspects, either alone or in combination, as applicable: the excitation beam may have a focal point that is laterally within the focal zone of the interrogation beam; the interrogation beam may have a focal point that is laterally within the focal zone of the excitation beam; there may be a camera that calculates an image of the sample based on the returning portion of the interrogation beam; the excitation beam may be scanned through the sample while the interrogation beam is stationary; the interrogation beam may be scanned through the sample while the excitation beam is stationary; and each of the interrogation beam and the excitation beam may be scanned through the sample concurrently.

According to other aspects, there is provided a method for interrogating the optical properties of a sample, which comprises generating photoacoustic signals within a sample; directing light towards a sample at a given location; collecting light from a sample at a given location; an array of photodetectors that detects collected light from the sample; a processor for collecting multiple acquisitions; and a processor for extracting differences between multiple acquisitions.

According to another aspect, there is provided camera-based photoacoustic remote sensing system (C-PARS) for imaging structures in a sample. The system comprises an excitation beam configured to generate absorption-induced ultrasonic signals in the sample at a multiplicity of excitation locations; an interrogation beam (spectrally-distinct from the excitation pulse) incident on the sample at least partially overlapping with the excitation illumination area, a portion of the interrogation beam returning from the sample and recorded by a camera with a multiplicity of optical detector elements; a system to generate a difference image by recording an interrogation beam image just before and just after pulsed excitation; a filter to remove excitation light and only capture interrogation light; an optical system (such as a multiplicity of lenses) to control the magnification and imaging field-of-view; and precise timing circuitry to control the excitation, interrogation, and recording timing.

According to other aspects, the images may be recorded with short exposures using shuttering or pulsed illuminations where exposure times are ideally on the order of the photoacoustic stress relaxation times of the absorbing targets (typically ~ns and <1 μs). For the "after" image, the interrogation beam may be pulsed (or the camera is shuttered) a small fixed delay (1-100 ns) after the excitation pulse. The pulsed excitation source may be replaced with an intensity-modulated excitation source. The modulation may be pulsed, a sequence of pulses or modulated with some other time-dependent modulation such as sinusoidal modulation, where the signal will be maximized when the modulation period is comparable to the stress relaxation time of the targets to be imaged (typically ~ns to <1 μs). A mean change in the absorption-induced scattered interrogation light may be detected to form a difference image between excitation illumination modulation patterns (one of these patterns could be no excitation). The pulsed interrogation source may be replaced with an intensity-modulated interrogation source. The difference image may be formed from images acquired using differing phase-shifts between excitation and interrogation intensity modulation patterns.

Other aspects will be apparent from the description and claims below.

BRIEF DESCRIPTION OF THE DRAWINGS

These and other features will become more apparent from the following description in which reference is made to the appended drawings, the drawings are for the purpose of illustration only and are not intended to be in any way limiting, wherein.

DETAILED DESCRIPTION OF PREFERRED EMBODIMENTS

Photoacoustic imaging is an emerging biomedical imaging modality that uses laser light to excite tissues. Energy absorbed by chromophores or any other absorber is converted to acoustic waves due to thermo-elastic expansion. These acoustic signals are detected and reconstructed to form images with optical absorption contrast. Photoacoustic imaging (PA) has been shown to provide exquisite images of microvessels and is capable of imaging blood oxygen saturation, gene expression, and contrast agents, among other uses. In most PA and ultrasound imaging systems piezoelectric transducers have been employed, in which an ultrasound coupling medium such as water or ultrasound gel is required. However for many clinical applications such as wound healing, burn diagnostics, surgery, and many endoscopic procedures physical contact, coupling, or immersion is undesirable or impractical. The system described herein is capable of in vivo photoacoustic imaging using non-contact non-interferometric sensing by a camera without use of any ultrasound medium.

The system described herein, a camera-based photoacoustic remote sensing (C-PARS) microscopy system, is based on the idea of sending a loosely focused excitation light to the sample and detecting photoacoustic signals using a confocal interrogation beam directed at the excitation spot. Preferably, the interrogation beam is spectrally distinct from the excitation beam or pulse. In addition, while the interrogation beam is preferably co-focused with the excitation spot, this may not always be the case, and adequate results may be achieved by having the interrogation beam incident on the sample immediately adjacent to the excitation spot, which may include at least a partial overlap with the excitation illumination area. Previous approaches for non-contact detection of photoacoustic signals used an optical detector such as interferometry or/and a photodiode to detect the reflected light at each scanning spot. In C-PARS a broad excitation and detection beam with mJ-J of pulse energy over a broad area is used. The reflected light from detection beam is mapped used a camera system over the entire field of view.

The excitation beam is preferably an intensity-modulated beam, which may include single pulses, a sequence of pulses, which may be regularly spaced or timed based on external events, or some other time-dependent modulation. The pulses or modulations may include square pulses, sinusoidal pulses or modulation, or other modulation techniques. In a sinusoidal modulation scheme, the signal may be maximized when the modulation period is comparable to the stress relaxation time of the targets to be imaged (typically ~ns to <1 µs). In this case, a mean change in the absorption-induced scattered interrogation light may be detected to form a difference image between excitation illumination modulation patterns, one of which could be no excitation.

Similarly, the interrogation source is preferably an intensity-modulated beam, which may include a single pulse, a sequence of pulses, which may be regularly spaced or timed based on external events, or some other time-dependent modulation. The interrogation beam will generally be dependent on the excitation beam, and the types of information that is being sought from the sample. For example, the interrogation beam may be timed to illuminate the sample before excitation, and immediately after excitation, or at different intervals after excitation. In some cases, it may be desirable to obtain a difference image formed by comparing images before and after excitation. For example, the difference image may be made from images acquired using differing phase-shifts between excitation and interrogation intensity modulation patterns. It may also be possible to use a lock-in technique on a sequence of images, where image sequences over time may be analyzed to lock-in to the excitation modulation rate. Various considerations for the intensity and relative timing of the excitation and interrogation beams will be apparent to those skilled in the art.

In the presently described system, a camera system is used to map the reflected light due to generated photoacoustic pressures over the entire field of view. The field of view can be defined by the size of the beams on the sample or field of view of the camera. The beams and camera can be scanned across the sample if necessary.

In one embodiment, a broad-area pulsed excitation beam is used and backreflected light changes are detected with a camera system to observe absorption-induced scattering and reflection changes over a large field of view.

Figure 10:
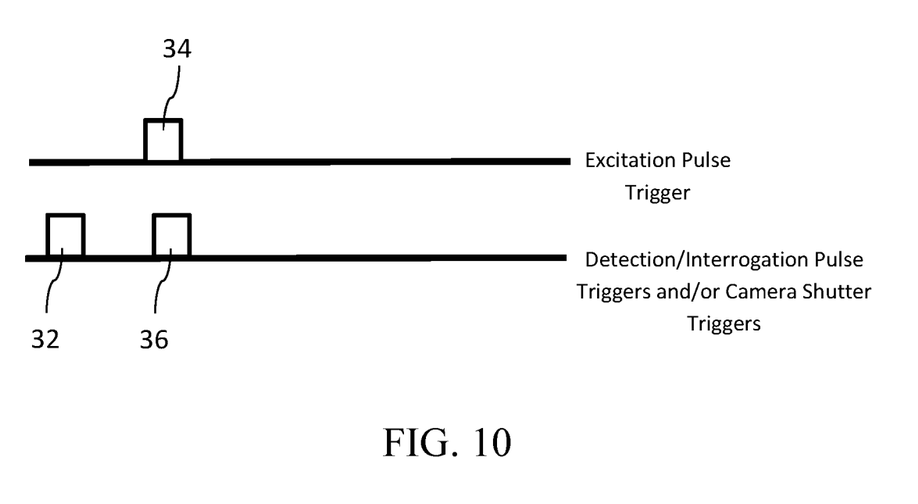
FIG. 10 is a pulse train representing the timing of triggering an excitation pulse compared to triggering a detection/interrogation pulse and/or a camera shutter.

This may be done by either using a continuous interrogation source and gating the camera detection to observe differences between before- and just-after pulsed excitation, or it could be accomplished using a pulsed interrogation light-source. A difference of the "before" and "just-after" pulsed excitation images may be used to reveal absorption-induced scattering changes. A filter front of the camera could be used to reject pulsed excitation light. Referring to FIG. 10, a pulse train representing sample timing for triggering an excitation pulse compared to triggering a detection or interrogation pulse and/or a camera shutter is shown. As shown, a first detection pulse or camera shutter trigger 32 occurs prior to the excitation pulse, providing a "before" image. Next, the excitation pulse 34 is triggered, and shortly thereafter a second detection pulse or camera shutter trigger 36 occurs to provide the "just after" image. These images are preferably recorded with short exposures using shuttering or pulsed illuminations, where exposure times are ideally on the order of the photoacoustic stress relaxation times of the absorbing targets (typically ~ns and <1 µs). For the "after" image, the interrogation beam is preferably pulsed, or the camera is shuttered, for a small fixed delay (1-100 ns) after the excitation pulse.

Preferably, the proposed approach may be used to obtain realtime reflection-mode imaging with optical absorption contrast over a large field of view.

Generated high initial photoacoustic pressures modifies scattering properties, such as scattering cross section of individual particles or reflectivity from larger structures in the sample. This results in time-varying intensity reflectivity which does not require phase sensitive detection. Rejecting interferometric effects leads to high signal to noise ratio detection. To observe such reflection modulations, the intensity changes of a probe beam in response to a generated photoacoustic initial pressure are measured. A non-interferometric approach with camera precludes any phase-modulation sensitivity to enable detection of intensity variations over the entire field of view. The proposed approach transiently amplifies existing refractive index steps where absorption is present.

The field of view will be principally determined by the excitation and interrogation beam illumination area. These light sources may be scanned to increase the field of view.

Lock-in detection may be used with a sequence of images to observe changes which are locked-in to the excitation repetition rate or modulation rate.

Deep-penetrating near-infrared light may be used for interrogation purposes to increase the depth of imaging into tissues.

C-PARS may be used to perform real time imaging on each pulse of excitation beam using a camera without need of optical, mechanical or ultrasound scanning. This is done by detecting photoacoustic signals using a confocal interrogation beam co-focused and co-scanned with the excitation spot. Local initial pressures are very large when optical focusing and thermal confinement conditions are applied. These large initial pressures can cause significant refractive index mismatch regions which are measured by the C-PARS system as changes in reflected light.

In various configurations, both beam may be fixed or scanned together, one beam may be fixed while the other beam can be scanned, the sample may be scanned while both beam are fixed, the sample may be scanned while both beam are scanning, or the sample may be scanned while one beam is fixed and the other is scanning.

It will be understood that the components described herein may be replaced with different components that perform similar functions to achieve similar results. For example, other examples may include all-fiber architectures. Other alternatives may include various coherence length sources. The various types of equipment available will be known to those skilled in the art, and it will be understood that the equipment described herein are merely provided as convenient or representative examples, and that the various possible embodiments will not be limited to the specific types described herein.

The C-PARS system takes advantage of optical excitation and detection which can help dramatically reduce the footprint of the system. By making the system all optical, a bulky ultrasound transducer can be omitted, making the system suitable for integrating with other optical imaging systems. As such, the C-PARS system may be made to provide in vivo real time imaging over a large field of view.

During in vivo imaging experiments, no agent or ultrasound coupling medium are required. However the target may be prepared with water or any liquid such as oil before non-contact imaging session.

Other advantages that are inherent to the structure will be apparent to those skilled in the art.

A pulse laser is used to generate photoacoustic signals and the acoustic signatures are interrogated using either a long-coherence or short-coherence length probe beam. The C-PARS system is utilized to remotely record the large local initial pressures from chromophores and without appreciable acoustic loses due to diffraction, propagation and attenuation.

The excitation beam may be any pulsed or modulated source of electromagnetic radiation, such as lasers or other optical sources. In one example, a nanosecond-pulsed laser was used. The excitation beam may be set to any wavelength suitable for taking advantage of optical (or other electromagnetic) absorption of the sample. The source may be monochromatic or polychromatic.

The interrogation beam may be any pulsed, continuous or modulated source of electromagnetic radiation including lasers or other optical sources. Any wavelength can be used for interrogation purpose depends on the application.

C-PARS may be used for either optical resolution photoacoustic microscopy (OR-PAM) or common photoacoustic microscopy (PAM).

In one example, both excitation and receiver beam may be combined and fixed or scanned on the sample. In this way, photoacoustic excitations may be mapped by a camera in the same area as they are generated and where they are the largest. Other arrangements may also be used, including keeping the receiver beam fixed while scanning the excitation beam or vice versa.

The excitation beam and sensing/receiver beam can be combined as is known by those skilled in the art, such as by using dichroic mirrors, prisms, beamsplitters, polarizing beamsplitters etc. They can also be focused using different optical paths.

The reflected light may be collected by any suitable detector, such as CMOS cameras, CCD cameras (including EM-CCD, intensified-CCDs, back-thinned and cooled CCDs), etc.

C-PARS may be used for A, B or C scan images for in vivo, ex vivo or phantom studies.

A multi-wavelength visible laser source may also been implemented to generate photoacoustic signals for functional or structural imaging.

C-PARS may be optimized in order to takes advantage of a multi-focus design for improving the depth-of-focus of 2D and 3D imaging. The chromatic aberration in the collimating and objective lens pair may be harnessed to refocus light from a fiber into the object so that each wavelength is focused at a slightly different depth location. Using these wavelengths simultaneously may be used to improve the depth of field and signal to noise ratio (SNR) of C-PARS images. During C-PARS imaging, depth scanning by wavelength tuning may be performed to image deeper structures in a sample. For example, deeper scanning may be achieved by using near-infrared wavelengths.

Polarization analyzers may be used to decompose detected light into respective polarization states. The light detected in each polarization state may provide information about ultrasound-tissue interaction.

EXAMPLES

Example arrangements of components for C-PARS will now be described. It will be understood that these examples are not limiting, and other arrangements of components may be used consistent with the principles described herein.

Figure 1:
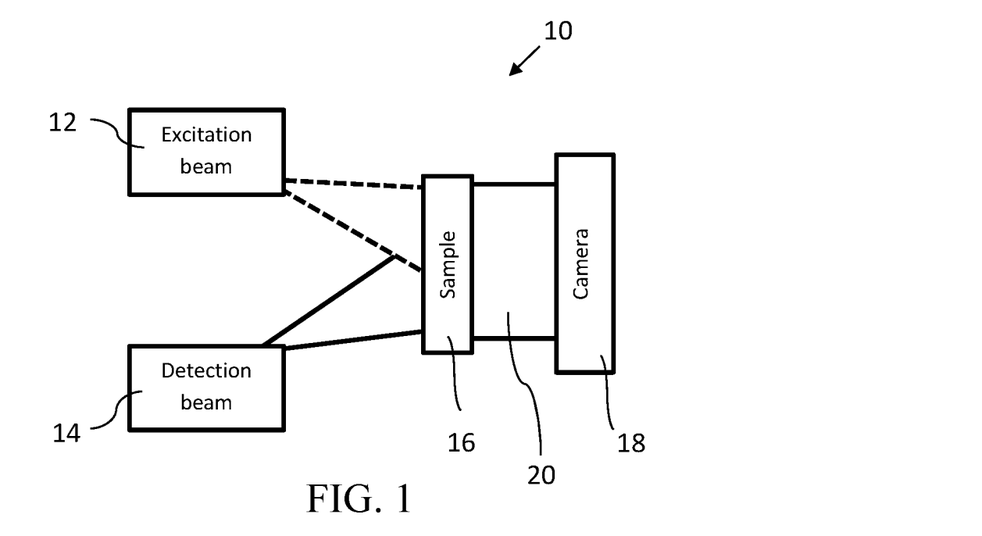
FIG. 1 is a block diagram of a generic C-PARS system with a detector that detects transmitted light.
Figure 2:
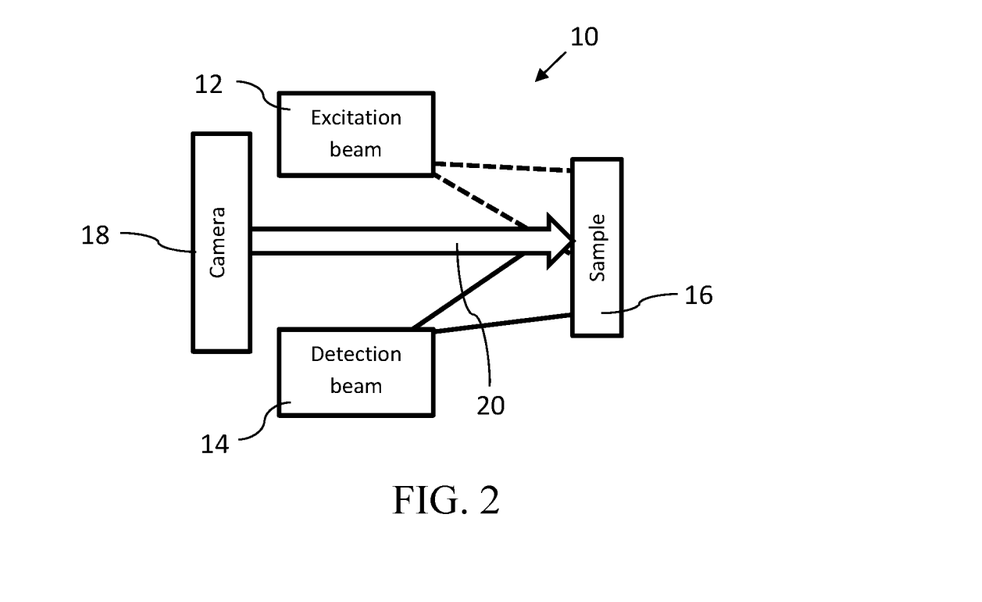
FIG. 2 is a block diagram of a generic C-PARS system with a detector that detects reflected light.
Figure 3:
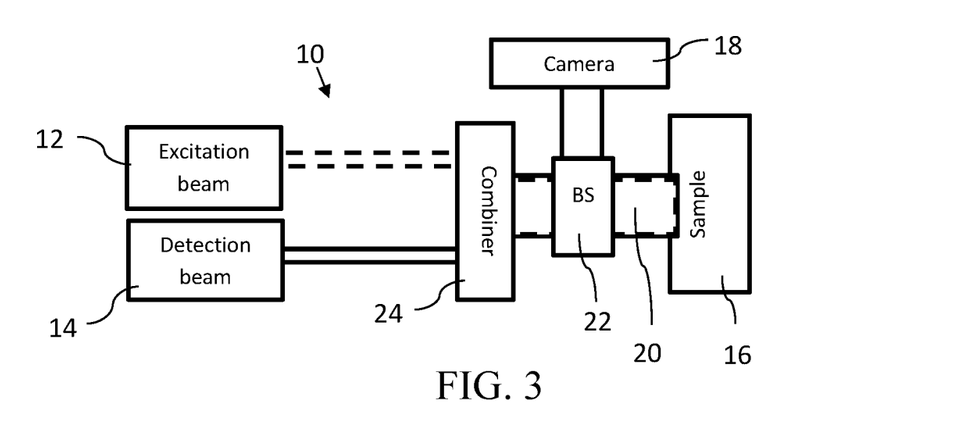
FIG. 3 through 9 are block diagrams of a C-PARS system with the excitation beam, the detection beam, and the detector in different positions relative to the sample and the propagation of the beams.

Referring to FIG. 1, a generic C-PARS system 10 of the transmission type is shown. Excitation beam 12 and detection beam 14 are both incident on sample 16, and camera 18 detects the resulting energy 20 transmitted through the sample 16. Referring to FIG. 2, a C-PARS system 10 of the reflection type is shown. Excitation beam 12 and detection beam 14 are incident on sample 16, and camera 18 detects the resulting energy 20 reflected from the sample 16.

Figure 4:
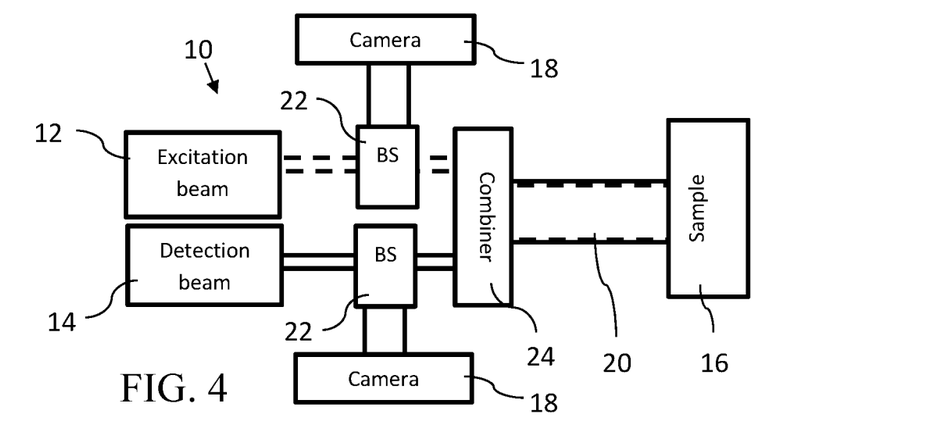
Figure 5:
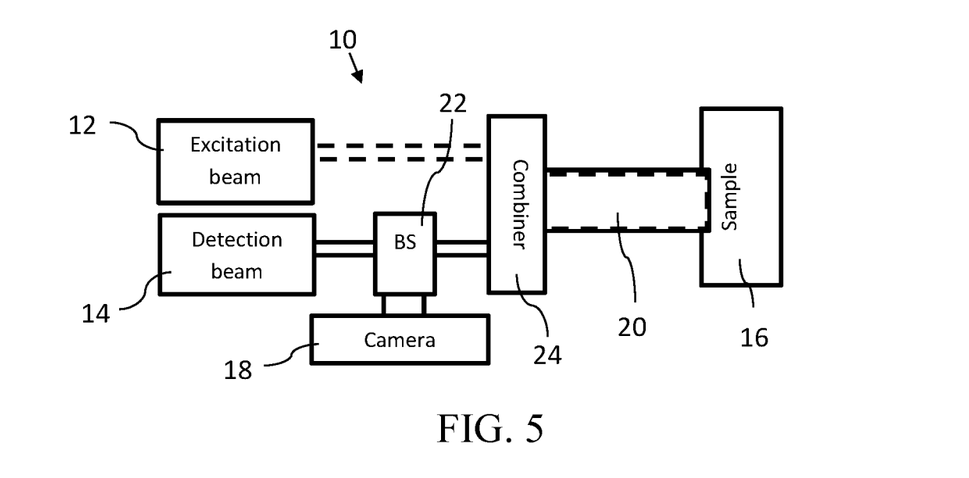
Figure 6:
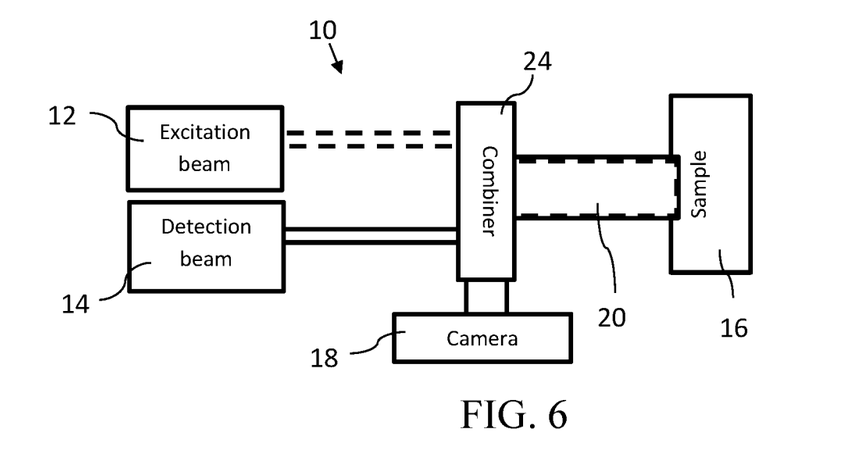
Figure 7:
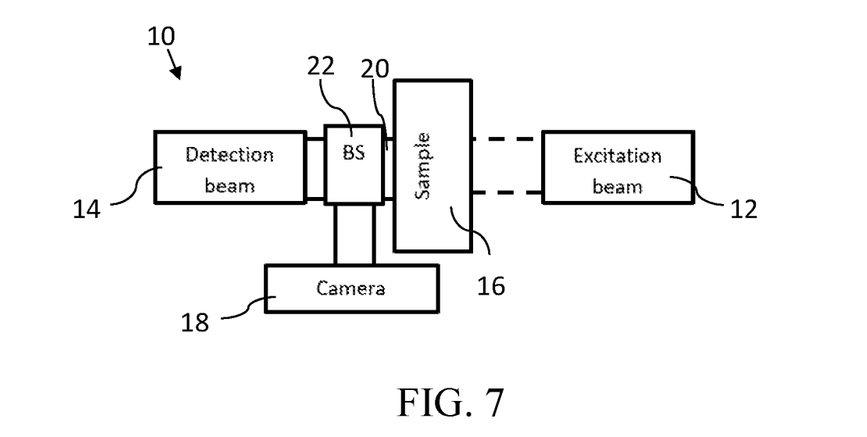

Referring to FIG. 3, FIG. 4, FIG. 5, FIG. 7, and FIG. 8, a beam splitter 22 may be used to direct the resulting energy 20 to the camera 18. Beam splitter 22 may be placed in a variety of locations depending on where camera 18 is located. Referring to FIG. 3, FIG. 4, FIG. 5, and FIG. 6, and FIG. 9, a combiner 24 may also be used to focus the excitation beam 12 and detection beam 14 toward sample 16. In the example shown in FIG. 3, combiner 24 is placed between the excitation and detection beams 12 and 14, and beam splitter 22 is placed along the path of the resulting energy 20 to direct resulting energy 20 into camera 18. Referring to FIG. 4, combiner 24 is placed between the excitation and detection beams 12 and 14, and beam splitter 22 is placed along the path of both the excitation beam 12 and the detection beam 14. In this example combiner 24 directs resulting energy 20 back toward combiner 24. The reflected resulting energy 20 is detected along the path of detection beam 14, while the excitation beam 12 is monitored along the path of excitation beam 12, providing further information on the excitation beam, such as the wavelength used. Referring to FIG. 5, combiner 24 is placed between the excitation and detection beams 12 and 14, and beam splitter 22 is placed along the path of the detection beam 14. In this example combiner 24 directs direct resulting energy 20 back toward detection beam 14, where it passes into camera 18. Referring to FIG. 6, a similar arrangement to the one shown in FIG. 4 is provided. In this case combiner 24 has an integrated beam splitter, and resulting energy 20 is directed to camera 18 when it returns to combiner 24 from sample 16. Referring to FIG. 7, depending on the type of sample 16, excitation beam 12 and detection beam 14 may also be positioned on opposite sides of sample 16. In this example, excitation beam 12 is directed to a first side of sample 16, detection beam 14 is directed to a second side of sample 16, and the resulting energy 20 is reflected from sample 16 toward detection beam 14, where it is directed by beam splitter 22 toward camera 18.

Figure 8A:
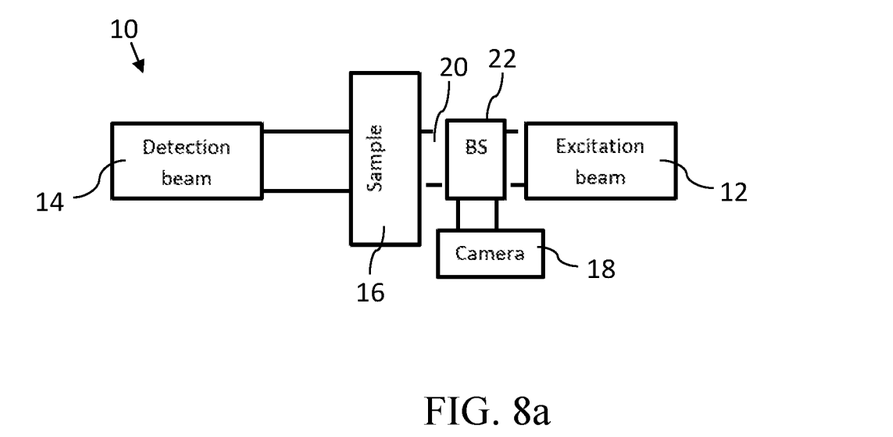
Figure 8B:
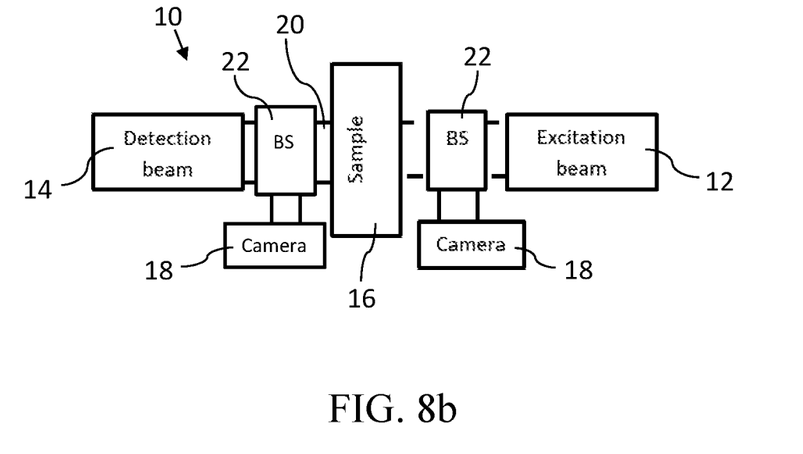
Figure 9:
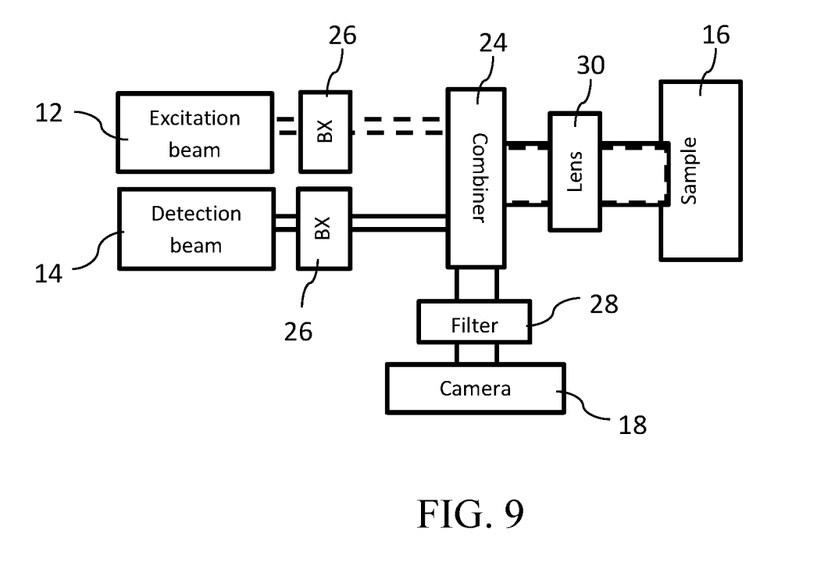

Referring to FIG. 8a, when the C-PARS system 10 is of the transmission type, excitation beam 12 is directed to a first side of sample 16, detection beam 14 is directed to a second side of sample 16, and the resulting energy 20 is transmitted through sample 16 toward excitation beam 12, where it is directed by beam splitter 22 toward camera 18. Referring to FIG. 8b, a similar arrangement may be used when the C-PARS system 10 is of the reflection type, with resulting energy 20 being reflected from sample 16 toward detection beam 14 before being diverted by beam splitter 22 toward camera 18. In this case, excitation beam 12 is also measured by a camera 18 positioned along the path of excitation beam 12. Referring to FIG. 9, any of the above arrangements of components may also include additional optical elements as shown. For example, these elements may include beam expanders 26, filters 28, and lenses 30. Other optical elements may additionally be used to direct and control the beams, as is known in the art. Filters 28 are used to filter non-desired wavelengths, such as filtering the wavelength of the excitation beam, or only transmitting the wavelength of the interrogation beam. Various optical elements, such as lenses, beam splitters, etc., whether depicted or not, may be included to control the magnification and imaging field-of-view, as required.

C-PARS Mechanism

Rather than calculate the phase shifts of transmitted light, C-PARS is interested in the amplitude of light reflected from a refractive index mismatch perturbed by photoacoustic pressures. With a large initial pressure, a significant refractive index step change in the confined excitation volume occurs. This results in a large amplitude reflection coefficient.

Refractive index changes from their unperturbed state can occur due to pressure rises. Initial pressures generated by the absorption of an optical excitation pulse which is shorter in time than the stress confinement and thermal confinement condition is described by $p_0 = \Gamma \phi \mu_a$ where $\Gamma$ is a material property known as the Grüneissen parameter, $\phi$ is the focal fluence of the excitation beam and $\mu_a$ is the optical absorption of the medium at the given excitation wavelength. These pressures can be large. As an example, assuming a focal fluence of 500 mJcm$^{-2}$, a whole blood sample (with a hemoglobin concentration of 150 gL$^{-1}$ assuming a fully oxygenated sample) with optical absorption at 532 nm excitation of 237 cm$^{-1}$ and a Grüneissen parameter of 1 gives an initial pressure of 119 MPa. These pressures are sufficient to create a measureable change in the refractive index which follows the elasto-optic relation such that the perturbed refractive index $(n^*(r,t))$ is related to the unperturbed refractive index $(n(r,t))$ and the pressure field $(p(r,t))$ by $n^*(r,t) = n[1 + (\eta n^2 p / 2\rho v_s^2)]$ where $\eta$ is the elasto-optic coefficient, $\rho$ is the specific density and $v_s$ is the speed of sound.

When the sample consists of a planar interface (where the curvature of the surface is much larger than the probe beam focal spot size) the small changes in refractive index can produce changes in the reflectivity of the probe beam. This can be modeled by taking the difference in the intensity reflection coefficients of the perturbed $$\left( R^* = \left| \frac{n_1 + \delta n - n_2}{n_1 + \delta n + n_2} \right|^2 \right)$$

and unperturbed $$\left( R_s = \left| \frac{n_1 - n_2}{n_1 + n_2} \right|^2 \right)$$

interfaces such that the measured signal varies with amplitude following $\Delta R = R^* - R_s$ where $n_1$ is the refractive index of the optical absorbing medium and $n_2$ is the refractive index of the optically transparent medium. Assuming that the perturbation is small such that $\delta n \ll 1$; $\delta n \ll n_1$, $n_2$ and that the refractive indices are all mostly real (this is not a requirement, but merely allows for intuitive approximation) provides an expression following $$\Delta R = 4 \delta n R_s \frac{n_2}{n_1^2 - n_2^2} + O\{\delta n\}$$

where $O\{\delta n\}$ represents higher order terms. This describes a linear relationship with the static reflectivity (due to the initial refractive index mismatch between $n_1$ and $n_2$) and a linear relationship with the perturbation $\delta n$ which is in turn proportional to the photoacoustic initial pressure.

In the case of an object, or a collection of objects which are optically scattering, optically absorbing, and are on the scale of or smaller than the beam spot size, optical property changes are more appropriately described by scattering theory. The refractive index modulation brought on by the photoacoustic initial pressures now is assumed to alter the scattering properties of individual particles. For the case of single particle interactions this can be observed as a change in the collected fraction (or observed reflection) such that $\Delta R_c = R^*_c - R_{s,c}$ where $R^*_c$ is the modified collected fraction and $R_{s,c}$ is the unperturbed collected fraction. In brief these describe a relationship which follows $\Delta R_c \propto \Delta \sigma_s$ where $$\Delta\sigma_s = 2\delta n_s \sigma_s \left( \frac{n_s - n_b}{|n_s - n_b|^2} - 1 \right) + O\{\delta n\}$$

is the change in the scattering cross-section of the particle, $n_s$ is the unperturbed refractive index of the particle, $\delta n_s$ is the refractive index change brought on by the elasto-optic effect, $n_b$ is the refractive index of the background medium and $\sigma_s$ is the unperturbed scattering cross section. In the case of a large ensemble of particles, the change in diffuse reflection is instead monitored which is described by radiative transfer theory in which individual particles are assumed to form an equivalent homogenous scattering medium with a perturbed and unperturbed set of optical scattering properties.

The system is sensitive to intensity reflectivity modulations at any depth within the probe beam optical depth-of-focus. Such modulations effectively begin instantaneously, coincident with the excitation pulse, irrespective of depth. Because the proposed system reads out phase-insensitive intensity reflectivity, time-resolved signals do not produce depth-resolved information.

Applications

It will be understood that the system described herein may be used in various ways, such as those purposes described in the prior art, and also may be used in other ways to take advantage of the aspects described above. A non-exhaustive list of applications is discussed below.

The system may be used for imaging angiogenesis for different pre-clinical tumor models.

The system may also be used for clinical imaging of micro- and macro-circulation and pigmented cells, which may find use for applications such as in (1) the eye, potentially augmenting or replacing fluorescein angiography; (2) imaging dermatological lesions including melanoma, basal cell carcinoma, hemangioma, psoriasis, eczema, dermatitis, imaging Mohs surgery, imaging to verify tumor margin resections; (3) peripheral vascular disease; (4) diabetic and pressure ulcers; (5) burn imaging; (6) plastic surgery and microsurgery; (7) imaging of circulating tumor cells, especially melanoma cells; (8) imaging lymph node angiogenesis; (9) imaging response to photodynamic therapies including those with vascular ablative mechanisms; (10) imaging response to chemotherapeutics including anti-angiogenic drugs; (11) imaging response to radiotherapy.

The system may be useful in estimating oxygen saturation using multi-wavelength photoacoustic excitation and C-PARS detection and applications including: (1) estimating venous oxygen saturation where pulse oximetry cannot be used including estimating cerebral venous oxygen saturation and central venous oxygen saturation. This could potentially replace catheterization procedures which can be risky, especially in small children and infants.

Oxygen flux and oxygen consumption may also be estimated by using C-PARS imaging to estimate oxygen saturation, and an auxiliary method to estimate blood flow in vessels flowing into and out of a region of tissue.

The system may also have some gastroenterological applications, such as imaging vascular beds and depth of invasion in Barrett's esophagus and colorectal cancers. Depth of invasion is key to prognosis and metabolic potential. Gastroenterological applications may be combined or piggy-backed off of a clinical endoscope and the miniaturized C-PARS system may be designed either as a standalone endoscope or fit within the accessory channel of a clinical endoscope.

The system may have some surgical applications, such as functional imaging during brain surgery, use for assessment of internal bleeding and cauterization verification, imaging perfusion sufficiency of organs and organ transplants, imaging angiogenesis around islet transplants, imaging of skin-grafts, imaging of tissue scaffolds and biomaterials to evaluate vascularization and immune rejection, imaging to aid microsurgery, guidance to avoid cutting critical blood vessels and nerves.

Other examples of applications may include CS-PARS imaging of contrast agents in clinical or pre-clinical applications; identification of sentinel lymph nodes; non- or minimally-invasive identification of tumors in lymph nodes; imaging of genetically-encoded reporters such as tyrosinase, chromoproteins, fluorescent proteins for pre-clinical or clinical molecular imaging applications; imaging actively or passively targeted optically absorbing nanoparticles for molecular imaging; and imaging of blood clots and potentially staging the age of the clots.

In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

The scope of the following claims should not be limited by the preferred embodiments set forth in the examples above and in the drawings, but should be given the broadest interpretation consistent with the description as a whole.

The invention claimed is:

1. A system for photoacoustic remote sensing for imaging a sample, comprising:
    one or more lasers configured to generate an excitation beam incident on the sample at an excitation location, the excitation beam being configured to be absorbed by the sample and induce changes in scattering properties of the sample;
    wherein the one or more lasers are configured to generate an interrogation beam incident on the sample at a detection location, at least a portion of the detection location being collocated with or adjacent to the excitation location; and
    a camera that is oriented toward the detection location to obtain optical images, the optical images comprising scattered portions of the interrogation beam detected simultaneously from a plurality of distinct points within the detection location, wherein the system is used in one or more of the following applications:
    imaging angiogenesis for pre-clinical tumor models;
    estimating oxygen saturation using multi-wavelength photoacoustic excitation;
    estimating venous oxygen saturation where pulse oximetry cannot be used;
    estimating cerebrovenous oxygen saturation and/or central venous oxygen saturation;
    estimating oxygen flux and/or oxygen consumption;
    estimating blood flow in vessels flowing into and out of a region of tissue;
    clinical imaging of micro- and macro-circulation and pigmented cells;
    imaging of the eye;
    augmenting or replacing fluorescein angiography;
    imaging dermatological lesions;
    imaging melanoma;
    imaging basal cell carcinoma;
    imaging hemangioma;

imaging psoriasis;
imaging eczema;
imaging dermatitis;
imaging Mohs surgery;
imaging to verify tumor margin resections;
imaging peripheral vascular disease;
imaging diabetic and/or pressure ulcers;
burn imaging;
plastic surgery;
microsurgery;
imaging of circulating tumor cells;
imaging melanoma cells;
imaging lymph node angiogenesis;
imaging response to photodynamic therapies;
imaging response to photodynamic therapies having vascular ablative mechanisms;
imaging response to chemotherapeutics;
imaging response to anti-angiogenic drugs;
imaging response to radiotherapy;
imaging vascular beds and depth of invasion in Barrett's esophagus and/or colorectal cancers;
functional imaging during brain surgery;
assessment of internal bleeding and/or cauterization verification;
imaging perfusion sufficiency of organs and/or organ transplants;
imaging angiogenesis around islet transplants;
imaging of skin-grafts;
imaging of tissue scaffolds and/or biomaterials to evaluate vascularization and/or immune rejection;
imaging to aid microsurgery;
guidance to avoid cutting blood vessels and/or nerves;
imaging of contrast agents in clinical or pre-clinical applications;
identification of sentinel lymph nodes;
non- or minimally-invasive identification of tumors in lymph nodes;
imaging of genetically-encoded reporters, wherein the genetically-encoded reporters include tyrosinase, chromoproteins, and/or fluorescent proteins for pre-clinical or clinical molecular imaging applications;
imaging actively or passively targeted optically absorbing nanoparticles for molecular imaging;
imaging of blood clots;
staging an age of blood clots;
replacing a catheterization procedure;
gastroenterological applications;
single-excitation pulse imaging over an entire field of view;
imaging of tissue;
imaging of cells;
imaging of scattered light from object surfaces;
imaging of absorption-induced changes of scattered light; or
non-contact imaging of optical absorption.

2. A system for photoacoustic remote sensing for imaging a sample, comprising:
one or more lasers configured to generate an excitation beam incident on the sample at an excitation location, the excitation beam being configured to be absorbed by the sample and induce changes in scattering properties of the sample;
wherein the one or more lasers are configured to generate an interrogation beam incident on the sample at a detection location, at least a portion of the detection location being collocated with or adjacent to the excitation location; and
an array of photo detectors that is oriented toward the detection location to obtain optical images, the optical images comprising scattered portions of the interrogation beam detected simultaneously from a plurality of distinct points within the detection location, wherein the system is used in one or more of the following applications:
imaging angiogenesis for pre-clinical tumor models;
estimating oxygen saturation using multi-wavelength photoacoustic excitation;
estimating venous oxygen saturation where pulse oximetry cannot be used;
estimating cerebrovenous oxygen saturation and/or central venous oxygen saturation;
estimating oxygen flux and/or oxygen consumption;
estimating blood flow in vessels flowing into and out of a region of tissue;
clinical imaging of micro- and macro-circulation and pigmented cells;
imaging of the eye;
augmenting or replacing fluorescein angiography;
imaging dermatological lesions;
imaging melanoma;
imaging basal cell carcinoma;
imaging hemangioma;
imaging psoriasis;
imaging eczema;
imaging dermatitis;
imaging Mohs surgery;
imaging to verify tumor margin resections;
imaging peripheral vascular disease;
imaging diabetic and/or pressure ulcers;
burn imaging;
plastic surgery;
microsurgery;
imaging of circulating tumor cells;
imaging melanoma cells;
imaging lymph node angiogenesis;
imaging response to photodynamic therapies;
imaging response to photodynamic therapies having vascular ablative mechanisms;
imaging response to chemotherapeutics;
imaging response to anti-angiogenic drugs;
imaging response to radiotherapy;
imaging vascular beds and depth of invasion in Barrett's esophagus and/or colorectal cancers;
functional imaging during brain surgery;
assessment of internal bleeding and/or cauterization verification;
imaging perfusion sufficiency of organs and/or organ transplants;
imaging angiogenesis around islet transplants;
imaging of skin-grafts;
imaging of tissue scaffolds and/or biomaterials to evaluate vascularization and/or immune rejection;
imaging to aid microsurgery;
guidance to avoid cutting blood vessels and/or nerves;
imaging of contrast agents in clinical or pre-clinical applications;
identification of sentinel lymph nodes;
non- or minimally-invasive identification of tumors in lymph nodes;
imaging of genetically-encoded reporters, wherein the genetically-encoded reporters include tyrosinase, chromoproteins, and/or fluorescent proteins for pre-clinical or clinical molecular imaging applications;

imaging actively or passively targeted optically absorbing nanoparticles for molecular imaging;
imaging of blood clots;
staging an age of blood clots;
replacing a catheterization procedure;
gastroenterological applications;
single-excitation pulse imaging over an entire field of view;
imaging of tissue;
imaging of cells;
imaging of scattered light from object surfaces;
imaging of absorption-induced changes of scattered light; or
non-contact imaging of optical absorption.

3. The system of claim 2, wherein the array of photo detectors comprises an optical camera.

4. The system of claim 2, further comprising a controller configured to control the excitation beam, the interrogation beam, and the array of photodetectors, wherein the controller is configured to activate the interrogation beam and the array of photo detectors to detect images before and after the excitation beam is activated.

5. The system of claim 2, wherein the excitation beam has a wavelength that is different than a wavelength of the interrogation beam.

6. The system of claim 2, wherein the interrogation beam has a power density that is sufficiently low to have a negligible impact on the scattering properties of the sample as detected by the array of photo detectors.

7. The system of claim 2, wherein the detection location is collocated with the excitation location and has an area equal to or greater than an area of the excitation location.

8. The system of claim 2, wherein the array of photo detectors detects a portion of scattered light that is transmitted through the sample.

9. The system of claim 2, wherein the array of photo detectors detects a portion of scattered light that is reflected from the sample.

10. The system of claim 2, wherein the sample is tissue.

11. The system of claim 2, wherein the system does not include an ultrasound transducer.

12. The system of claim 2, wherein a wavelength of the excitation beam is any wavelength configured for optical or electromagnetic absorption by the sample.

13. The system of claim 2, wherein the system does not detect surface oscillations from the sample.

14. The system of claim 2, wherein the one or more lasers includes an excitation laser configured to generate the excitation beam, and includes an interrogation laser configured to generate the interrogation beam.

15. A method of imaging a sample using photoacoustic remote sensing, the method comprising the steps of:
inducing changes in scattering properties of the sample by exciting the sample at an excitation location using an excitation beam;
directing an interrogation beam onto a detection location of the sample, at least a portion of the detection location being collocated with or adjacent to the excitation location; and
obtaining one or more images of the sample using an array of photo detectors that detects scattered portions of the interrogation beam, the interrogation beam being detected simultaneously from a plurality of distinct points within the detection location, wherein the one or more images are used in one or more of the following applications:
imaging angiogenesis for pre-clinical tumor models;
estimating oxygen saturation using multi-wavelength photoacoustic excitation;
estimating venous oxygen saturation where pulse oximetry cannot be used;
estimating cerebrovenous oxygen saturation and/or central venous oxygen saturation;
estimating oxygen flux and/or oxygen consumption;
estimating blood flow in vessels flowing into and out of a region of tissue;
clinical imaging of micro- and macro-circulation and pigmented cells;
imaging of the eye;
augmenting or replacing fluorescein angiography;
imaging dermatological lesions;
imaging melanoma;
imaging basal cell carcinoma;
imaging hemangioma;
imaging psoriasis;
imaging eczema;
imaging dermatitis;
imaging Mohs surgery;
imaging to verify tumor margin resections;
imaging peripheral vascular disease;
imaging diabetic and/or pressure ulcers;
burn imaging;
plastic surgery;
microsurgery;
imaging of circulating tumor cells;
imaging melanoma cells;
imaging lymph node angiogenesis;
imaging response to photodynamic therapies;
imaging response to photodynamic therapies having vascular ablative mechanisms;
imaging response to chemotherapeutics;
imaging response to anti-angiogenic drugs;
imaging response to radiotherapy;
imaging vascular beds and depth of invasion in Barrett's esophagus and/or colorectal cancers;
functional imaging during brain surgery;
assessment of internal bleeding and/or cauterization verification;
imaging perfusion sufficiency of organs and/or organ transplants;
imaging angiogenesis around islet transplants;
imaging of skin-grafts;
imaging of tissue scaffolds and/or biomaterials to evaluate vascularization and/or immune rejection;
imaging to aid microsurgery;
guidance to avoid cutting blood vessels and/or nerves;
imaging of contrast agents in clinical or pre-clinical applications;
identification of sentinel lymph nodes;
non- or minimally-invasive identification of tumors in lymph nodes;
imaging of genetically-encoded reporters, wherein the genetically-encoded reporters include tyrosinase, chromoproteins, and/or fluorescent proteins for pre-clinical or clinical molecular imaging applications;
imaging actively or passively targeted optically absorbing nanoparticles for molecular imaging;
imaging of blood clots;
staging an age of blood clots;
replacing a catheterization procedure;
gastroenterological applications;
single-excitation pulse imaging over an entire field of view;
imaging of tissue;

imaging of cells;
imaging of scattered light from object surfaces;
imaging of absorption-induced changes of scattered light; or
non-contact imaging of optical absorption.

16. The method of claim 15, wherein the array of photo detectors comprises an optical camera.

17. The method of claim 15, further comprising detecting optical images of the detection location before and after the excitation beam is activated.

18. The method of claim 15, wherein the excitation beam has a wavelength that is different than a wavelength of the interrogation beam.

19. The method of claim 15, wherein the interrogation beam has a power density that is sufficiently low to have a negligible impact on the scattering properties of the sample as detected by the array of photo detectors.

20. The method of claim 15, wherein the detection location is collocated with the excitation location and has an area equal to or greater than an area of the excitation location.

21. The method of claim 15, wherein the array of photo detectors detects a portion of scattered light that is transmitted through the sample.

22. The method of claim 15, wherein the array of photo detectors detects a portion of scattered light that is reflected from the sample.

23. The method of claim 15, wherein obtaining one or more images of the sample includes non-interferometrically obtaining the one or more images of the sample.

24. A system for photoacoustic remote sensing for imaging a sample, comprising:
one or more lasers configured to generate an excitation beam incident on the sample at an excitation location, the excitation beam being configured to be absorbed by the sample and induce changes in scattering properties of the sample;
wherein the one or more lasers are configured to generate an interrogation beam incident on the sample at a detection location, at least a portion of the detection location being collocated with or adjacent to the excitation location; and
an array of photo detectors that is oriented toward the detection location to obtain optical images, the optical images comprising scattered portions of the interrogation beam detected simultaneously from a plurality of distinct points within the detection location, wherein:
the excitation beam is configured to generate absorption-induced ultrasonic signals in the sample at a multiplicity of excitation locations that define the excitation location;
the interrogation beam at least partially overlaps with the excitation location, a portion of the interrogation beam returning from the sample and recorded by the array of photo detectors;
the system further includes a processor configured to generate a difference image by recording an interrogation beam image before and after the absorption-induced ultrasonic signals are generated;
the system further includes a filter configured to selectively pass the interrogation beam returning from the sample;
the system further includes an optical system configured to control a magnification and an imaging field-of-view of the interrogation beam; and
the system further includes timing circuitry configured to control a timing of the excitation beam, the interrogation beam, and recording of the interrogation beam image.

25. The system of claim 24, wherein the excitation beam is pulsed or intensity-modulated.

26. The system of claim 24, wherein the interrogation beam is pulsed or intensity-modulated.

27. The system of claim 24, wherein a lock-in technique is used on a sequence of images, and the sequence of images over time is analyzed to lock-in to an excitation modulation rate.

* * * * *